(12) United States Patent
Huang et al.

(10) Patent No.: US 8,120,770 B2
(45) Date of Patent: Feb. 21, 2012

(54) THREE-DIMENSIONAL (3D) HYDRODYNAMIC FOCUSING USING A MICROFLUIDIC DEVICE

(75) Inventors: Tony Jun Huang, State College, PA (US); Xiaole Mao, State College, PA (US)

(73) Assignee: The Penn State Research Foundation, University Park, PA (US)

( * ) Notice: Subject to any disclaimer, the term of this patent is extended or adjusted under 35 U.S.C. 154(b) by 492 days.

(21) Appl. No.: 12/207,699

(22) Filed: Sep. 10, 2008

(65) Prior Publication Data

US 2009/0066936 A1    Mar. 12, 2009

Related U.S. Application Data

(60) Provisional application No. 60/971,054, filed on Sep. 10, 2007.

(51) Int. Cl.
*G01N 1/10* (2006.01)
(52) U.S. Cl. ............ 356/246; 436/180; 209/208
(58) Field of Classification Search ............ 356/246
See application file for complete search history.

(56) References Cited

U.S. PATENT DOCUMENTS

| | | | |
|---|---|---|---|
| 2004/0266022 A1* | 12/2004 | Sundararajan et al. | 436/180 |
| 2007/0117086 A1* | 5/2007 | Evans et al. | 435/4 |
| 2009/0014360 A1* | 1/2009 | Toner et al. | 209/208 |
| 2009/0323061 A1* | 12/2009 | Novotny et al. | 356/336 |

OTHER PUBLICATIONS

Ookawara, Shinichi, David Street and Kohei Ogawa, "Numerical study on development of particle concentration profiles in a curved microchannel", Chemical Engineering Science 61 (2006) pp. 3714-3724, available online Feb. 28, 2006.*

Mao, Xiaole, Waldeisen, John Robert, Huang, Tony Jun, "Microfluidic drifting"—implementing three-dimensional hydrodynamic focusing with a single-layer planar microfluidic device, Lab Chip, 2007, vol. 7, 1260-1262.

Shi, Jinjie, Mao, Xiaole, Ahmed, Daniel, Coletti, Ashley, Huang, Tony Jun, Focusing microparticles in a microfluidic channel with standing surface acoustic waves (SSAW), Lab Chip, 2008, vol. 8, 221-223.

Ottino, Julio M., Wiggins, Stephen, Introduction: mixing in microfluidics, Phil. Trans. R. Soc. Lond., 2004, 362, 923-935.

Chin, Curtis D., Linder, Vincent, Sia, Samuel K., Lab-on-a-chip devices for global health: Past studies and future opportunities, Lab Chip, 2007, vol. 7, 41-57.

Chaw, K.C., Manimaran, M., Tay, E.H., Swaminathan, S., Multi-step microfluidic device for studying cancer metastasis, Lab Chip, 2007, vol. 7, 1041-1047.

Simonnet, Claire, Groisman, Alex, Two-dimensional hydrodynamic focusing in a simple microfluidic device, Appl. Phys. Lett. 87, 114104 (2005).

(Continued)

*Primary Examiner* — Gregory J Toatley
*Assistant Examiner* — Rebecca C Slomski
(74) *Attorney, Agent, or Firm* — Gifford, Krass, Sprinkle, Anderson & Citkowski, P.C.

(57) ABSTRACT

A microfluidic device comprises inlets for a sample flow and an out-of-plane focusing sheath flow, and a curved channel section configured to receive the sample flow and out-of-plane focusing sheath and to provide hydrodynamic focusing of the sample flow in an out-of-plane direction, the out-of-plane direction being normal to a plane including the curved channel.

17 Claims, 8 Drawing Sheets

OTHER PUBLICATIONS

Chang, Chih-Chang, Huang, Zhi-Xiong, Yang, Ruey-Jen, Three-dimensional hydrodynamic focusing in a two-layer polydimethylsiloxane (PDMS) microchannels, J. Micromech. Microeng. 17 (2007) 1479-1486.

Sundararajan, Narayan, Pio, Michael S., Lee, Luke P., Berlin, Andrew A., Three-Dimensional Hydrodynamic Focusing in Polydimethylsiloxane (PDMS) Microchannels, Journal of Microelectromechanical Systems, vol. 13, No. 4, Aug. 2004.

Sudarsan, Arjun P., Ugaz, Victor, M., Multivortex micromixing, PNAS, 2006, vol. 103, No. 19, 7228-7233.

Yang, Ren, Feeback, Daniel L., Wang, Wanjun, Microfabrication and test of a three-dimensional polymer hydro-focusing unit for flow cytometry applications, Sensors and Actuators A 118 (2005) 259-267.

Wolff, A., Perch-Nielsen, R., Larsen, U.D., Friis, P., Granovic, G., Paulsen, C.R., Kutter, J.P., Telleman, P., Integrating advanced functionality in a microfabricated high-throughput fluorescent-activated cell sorter, Lab Chip, 2003, vol. 3, 22-27.

Mao, Xiaole, Waldeisen, John Robert, Juluri, Bala Krishna, Huang, Tony Jun, Hydrodynamically tunable optofluidic cylindrical microlens, Lab Chip, 2007, vol. 7, 1303-1308.

Howell, Peter B., Jr., Mott, David R., Golden, Joel P., Ligler, Frances S., Design and evaluation of a Dean vortex-based micromixer, Lab Chip, 2004, vol. 4, 663-669.

Sudarsan, Arjun P., Ugaz, Victor M., Fluid mixing in planar spiral microchannels, Lab Chip, 2006, vol. 6, 74-82.

* cited by examiner

US 8,120,770 B2

THREE-DIMENSIONAL (3D) HYDRODYNAMIC FOCUSING USING A MICROFLUIDIC DEVICE

REFERENCE TO RELATED APPLICATION

This application claims priority from U.S. Provisional Patent Application Ser. No. 60/971,054, filed Sep. 10, 2007, the entire content of which is incorporated herein by reference.

GOVERNMENT SUPPORT

This invention was made with government support under awarded by Contract No. ECCS-0609128 awarded by the National Science Foundation. The government has certain rights in the invention.

FIELD OF THE INVENTION

The present invention relates to hydrodynamic focusing.

BACKGROUND OF THE INVENTION

Hydrodynamic focusing is used to compress a sample flow, typically in two dimensions. Improved methods of hydrodynamic focusing would be useful for numerous applications, such as flow cytometry and single molecule fluorescence.

SUMMARY OF THE INVENTION

Three dimensional (3D) hydrodynamic focusing was achieved in a microfluidic device. A sample flow and a vertical focusing sheath flow were passed through a curved channel section, allowing hydrodynamic focusing (i.e. flow compression) of the sample flow in a direction normal to the plane of the sample flow, which may be normal to a substrate. This process may be termed microfluidic drifting. A second horizontally focusing sheath flow can be used to achieve hydrodynamic focusing in the plane of sample flow, orthogonal to the first focus direction, for example in a direction parallel to a substrate. Hence, a combination of these effects permits 3D hydrodynamic focusing to be readily achieved, giving a sample flow narrowed (compressed) both horizontally and vertically. The compressed flow allows improved analyte detection, chemical processing, biochemical processing, flow cytometry, chemical processing and the like, in particular allowing more reliable single molecule sensitivity in some applications.

In representative examples, the sample flow, vertical focusing sheath flow, and horizontally focusing sheath flow are all substantially coplanar, and may be parallel to a planar substrate, allowing substantial simplification of device fabrication. For the first time, 3D hydrodynamic focusing was achieved without need for any out-of-plane flow, allowing planar devices to be fabricated using a 2D lithographic process. Analyte throughput in the detection region is increased, and the probability of detecting an analyte in the sample flow is increased. These advantages are useful in a wide range of applications.

Hydrodynamic focusing devices using microfluidic drifting may be used in many applications which would otherwise be impractical or less accurate using conventional microfluidic approaches. For the first time, 3D hydrodynamic focusing was achieved using a single-layer planar microfluidic device, which can be fabricated using 2D lithography.

An example microfluidic device comprises a generally planar substrate supporting a sample flow inlet configured to receive a sample flow, a first flow inlet configured to receive a first sheath flow (there may optionally be other sheath flows), and a curved channel. The curved channel is configured to receive the sample flow and the first sheath flow and to provide out-of-plane hydrodynamic focusing of the sample flow, the sample flow being compressed along a direction normal to the substrate. Example devices are single layer microfluidic devices, in which the sample flow, the first sheath flow, and any additional sheath flows are generally coplanar. For example, in-plane hydrodynamic focusing sheath flows may be used to provide hydrodynamic focusing of the sample flow along a direction parallel to the substrate, the first sheath flow and the in-plane hydrodynamic focusing sheath flows together providing three-dimensional hydrodynamic focusing of the sample flow.

An example apparatus may include an output channel, the three-dimensional hydrodynamic focusing acting to compress the sample flow within a region near the center of the output channel, surrounded by the sheath flows. A radiation detector may be configured to detect radiation from the sample flow, and an excitation source may be configured to induce the radiation within the sample flow. Examples of the present invention include methods and apparatus for fluorescence detection of molecules and/or other fluorophores, including single-molecule fluorescence. Example apparatus include a flow cytometer, a fluorescence spectrometer, a laser spectrometer, a laminar mixer, a reaction vessel, or a chemical processing device, and may be multi-functional devices having one or more of such functions, and/or other functions.

A curved channel may have an inner side wall and an outer side wall, the side walls being generally normal to the substrate, the sample flow inlet and the first flow inlet being configured to introduced the sample flow and first sheath flow into the curved channel to initially have a fluid interface that is generally parallel to the side walls. As the sample flow and sheath flow progress through the curved channel, the fluid interface between them becomes highly curved, and the sample flow may the curved channel as a thin layer, narrowed in a direction normal to the substrate and extending across the width of the curved channel at the exit thereof. The sample flow may be introduced to the curved channel so as to be initially closer to the inner side wall, for example between the fluid interface with the first sheath flow and the inner side wall.

A method of hydrofluoric focusing a sample flow in a planar microfluidic device having a planar substrate comprises passing the sample flow and a sheath flow through a curved channel disposed on the planar substrate, the curved channel section providing hydrofluidic focusing of the sample flow in a direction generally normal to the planar substrate. The sample flow may be further passed through a linear channel section between a pair of in-plane focusing sheath flows, so as to obtain three-dimensional hydrofluoric focusing of the sample flow. The sample flow including biological cells, the method being a method of flow cytometry. The sample flow may include fluorescent molecules, the method being a method of single-molecule fluorescence spectroscopy. Other analytical methods may be improved by examples of the present invention.

BRIEF DESCRIPTION OF THE DRAWINGS

FIG. 2A shows a photomask used, FIG. 2B shows details of the hydrodynamic focusing section, and FIG. 2C shows a schematic of an optical setup for side-view epifluorescence imaging of the focused flow;

FIG. 3A is a top view of the sample flow pattern during the 3D focusing process, FIG. 3B is a CFD simulation under the same flow conditions, FIG. 3C is a side view of the 3D focused sample flow (flow direction: right to left) in the main channel, and FIG. 3D is the same view of the channel after the flow is stopped;

DETAILED DESCRIPTION OF THE INVENTION

Figure 1:
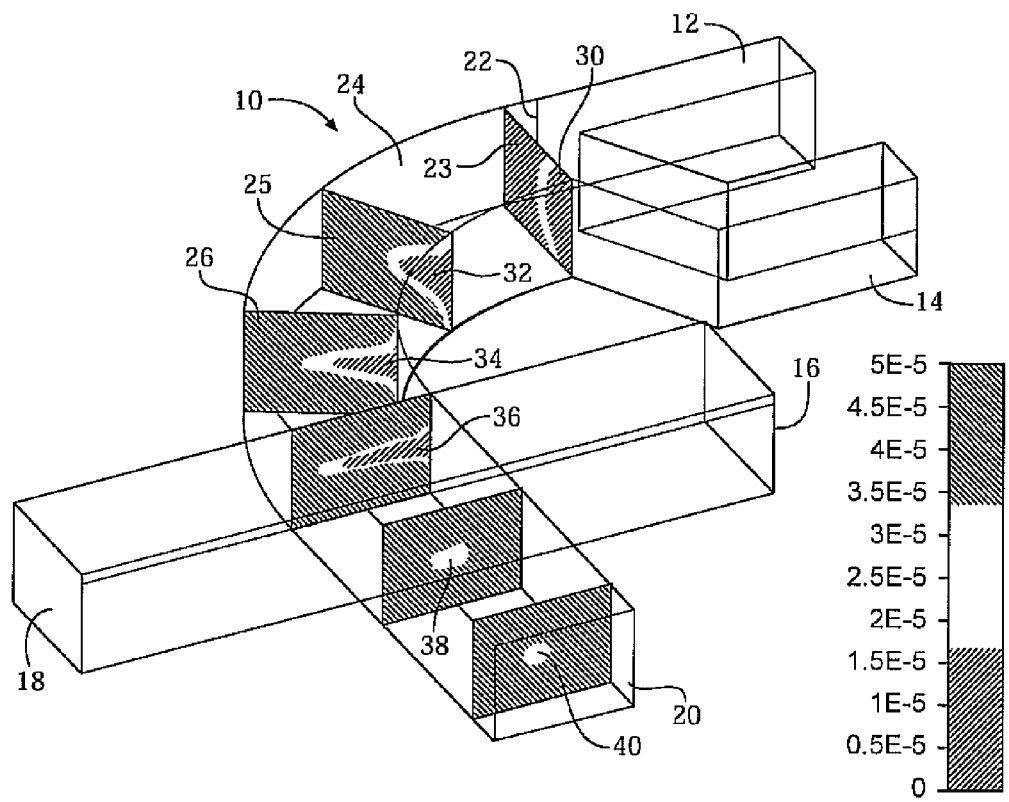
FIG. 1 is a schematic of a 3D hydrodynamic focusing process achieved using a "microfluidic drifting" technique, in which slices 1-10 are the cross-sectional profiles of the fluorescein dye concentration in the focusing device.

Hydrodynamic focusing can be used to compress a sample flow, typically in two dimensions. The focusing process can be used to increase sample throughput in the detection region, assisting characterization of the sample flow. In a conventional planar device, spreading of the sample flow in a vertical direction (here, the term vertical refers to a direction perpendicular to the plane of the sample flow) reduces characterization efficiency. In some applications, an analyte can be missed, particularly for flow cytometry and single molecule analysis methods. Improved techniques are required to give three dimensional (3D) hydrodynamic focusing.

A novel fluid manipulation technique termed "microfluidic drifting" was developed which allows 3D hydrodynamic focusing. A single-layer planar microfluidic device was fabricated that provided effective and robust 3D hydrodynamic focusing, without the need for any extensive fabrication technique other than standard soft lithography. A "microfluidic drifting" technique can be effectively used in focusing small molecules and also larger microparticles such as biological cells. "Microfluidic drifting" is readily applicable for 3D hydrodynamic focusing of biological cells for microfluidics based flow cytometry devices.

Embodiments of the present invention include apparatus and methods for hydrodynamic focusing. In some examples, microfluidic drifting based 3D hydrodynamic focusing comprises two steps. A sample flow can be focused in a first direction using the transverse Dean flow, and the sample flow can be focused in a second direction in horizontal plane using a sheath flow. The second direction may be parallel to a substrate plane, and in some examples may be referred to as the horizontal direction. The first direction may be normal to the substrate, and may be referred to as the vertical direction.

An example microfluidic device, operable to provide three-dimensional hydrodynamic focusing of a sample flow, includes a curved channel section operable to provide hydrodynamic focusing in an out-of-plane direction, relative to a plane including the curved channel. An in-plane sheath flow can then provide in-plane focusing, the combination of focusing effects cooperatively focusing the sample flow. The 3D focused sample flow is compressed, both in out of plane and in plane directions, relative to the incoming sample flow. Focusing in one or both planes may be selectively switched on or off as required, for example for use with different analytical techniques. For some applications, only out-of-plane focusing may be used, for example using a vertical focusing sheath flow and curved channel to compress the sample flow into a narrow horizontal band parallel to the substrate. A radiation beam may then be passed through the horizontal band, or other analytical technique used.

Planar microfluidic devices according to embodiments of the present invention may be used in various applications, such as a flow cytometer, single molecule detection based analysis, fluorescence spectrometer, other laser spectrometer, laminar mixer, micro-chemical reaction vessel, chemical or biochemical kinetics measuring device, or other analytical instrument or chemical processing device. Applications include controlled reaction vessels capable of controllably reacting individual molecules.

A curved channel can be used to provide out-of-plane focusing of the sample flow, by co-injection of a sample flow and a vertical focusing sheath flow into the curved channel. The sample flow and a vertical focusing sheath flow, have, for example, different densities. In examples described below, the curved channel section has a bend angle of 90 degrees. However, this example is not limiting and different bend angles may be used, for example in the range 10-180 degrees. The curved channel may be generally in a plane parallel to a supporting substrate, so that the focusing effect is generally out of the plane of the substrate. In some examples, the substrate may be flexible and/or curved, allowing other hydrodynamic effects to be obtained if desired.

An improved method of three-dimensional hydrofluoric focusing of a sample flow includes passing the sample flow through a curved channel along with a second flow of a different density, and further passing the sample flow through a fluid sheath crossing the sample flow, the curved channel and fluid sheath cooperatively providing three-dimensional hydrofluoric focusing of the sample flow.

An example microfluidic device includes a sample flow and a first sheath flow injected into a microfluidic channel. The adjacent injection of the flows into the channel initially results in an optically smooth, nearly vertical interface, due to the laminar flow that typically dominates in microfluidic channels. However, on entering a curved channel, the fluids experiences centrifugal force along the curved trajectory. Any fluid flowing in the middle of the channel (where the flow velocity is the highest) experiences a higher centrifugal force than the surrounding flow. As a result, a pair of secondary counter-rotating vortices (Dean vortices) located in the upper and lower half of the cross-sectional plane of the channel is induced, and the secondary vertical flow perturbs the fluidic interface. Fluid in the middle of channel is directed towards the outer channel wall, and fluid at the top and bottom of the channel is directed towards the inner channel wall. Consequently, an originally vertical fluidic interface bows outward, creating a curved interface. The magnitude of the centrifugal effect and consequent bowing of the interface is related to the ratio of inertial and centrifugal force to viscous force. The shape of the fluidic interface can be readily adjusted by changing the flow rate, so as to obtain a substantially vertically focused flow, the sample flow extending over most of the width of the curved channel, but focused in the center in the vertical direction. Once the fluids exit the 90-degree curve, the fluidic interface profile may be approximately static, before any significant distortion caused by diffusion and/or gravity. A horizontal sheathing flow can then used to obtain a fluid flow further focused in the horizontal plane, so that the sample flow is focused vertical and horizontally. In some examples of the present invention, horizontal focusing is optional, and may not be present.

FIG. 1 shows an example device for 3D focusing, the focusing mechanism being shown using a computational fluid dynamic (CFD) simulation (CFDACE+, ESI-CFD, Huntsville, Ala.). The figure shows an apparatus 10 with sample flow inlet 14, first sheath flow (vertical focusing sheath flow) inlet 12, curved channel 24, first horizontal focusing sheath flow inlet 16, second horizontal focusing sheath flow inlet 18, and flow outlet 20. The example device shown includes four inlets for sample and sheath flows, one outlet, and a curved channel with a 90-degree bend angle, in this example having a mean radius of 250 µm. The widths of channels for the sample flow and the vertical focusing sheath flow are 50 µm and the two side channels for horizontal focusing sheath flows are 100 µm wide. The width of the main channel (measured parallel to the substrate normal to the side walls) is 100 µm and the channel depth (measured normal to the substrate) throughout the entire device is 75 µm. Dimensions are exemplary, and other radii, bend angles, and/or channel dimensions may be used. The inlets and channels may be formed in any appropriate material, and may be supported by a planar substrate (not shown in FIG. 1 for illustrative clarity).

The 3D hydrodynamic focusing is accomplished in a two-step sequence. The first step focuses the sample flow in the vertical direction by using what may be termed a "microfluidic drifting" technique. This term refers to the lateral drift of the sample flow caused by the secondary flow (possibly through the action of Dean Vortices) induced by the centrifugal effect in the curve of microfluidic curved channel.

In FIG. 1, the sample flow (50 µM fluorescein dye solution, slice 1), and the vertical focusing sheath flow (water, slice 2) are co-infused into the 90-degree curve of the curved channel 24. The shading and bargraph represents fluorescein molar concentration. At the join 22 of the first sheath flow and sample flow, the flows are adjacent within the channel, and the boundary between the flows is vertical. In this context, the term vertical refers to the normal to the substrate and is used for convenience. However, use of this term is not intended to limit the orientation of the substrate. The figure shows a number of slices representing model flow configurations at that point, such as slice at 23 just within the curved channel 24. In the curved channel, the induced secondary flow causes the sample flow to drift laterally to the opposite side of channel (slices 5-8). The flow boundary becomes curved, with the flow profile showing the sample flow bulging into the sheath flow near the center of the flow channel, as shown at 30, 32, 34, and 36.

The final profile 36 of the drifted sample flow at the exit of the curved channel ("curve") is determined by the total flow rate through the curve as well as the flow rate ratio between the sample flow and vertical focusing sheath flow. By carefully controlling the total flow rate and flow rate ratio, the sample flow can be vertically focused into a thin horizontal flow sandwiched between the split vertical focusing sheath flows (at 36, slice 8). Focusing in the horizontal direction (slices 8-10) is conducted with two horizontal focusing sheath flows (water, slices 3 and 4) from inlets 16 and 18, which further compress the vertically focused sample flow from both sides. The combined effects of these two focusing steps result in a 3D hydrodynamically focused sample flow in the center of the microfluidic channel, shown at 38 and 40.

The compression ratios for both the vertical and horizontal focusing can be readily altered by changing the flow rates of the sample flow and sheath flows.

Figure 2A:
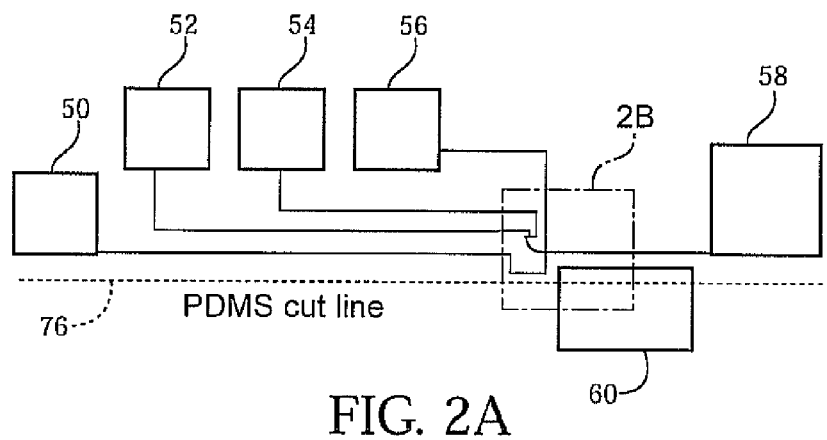
FIGS. 2A-2C illustrate a microfluidic device configuration for creating and characterizing a 3D focused flow, where
Figure 2B:
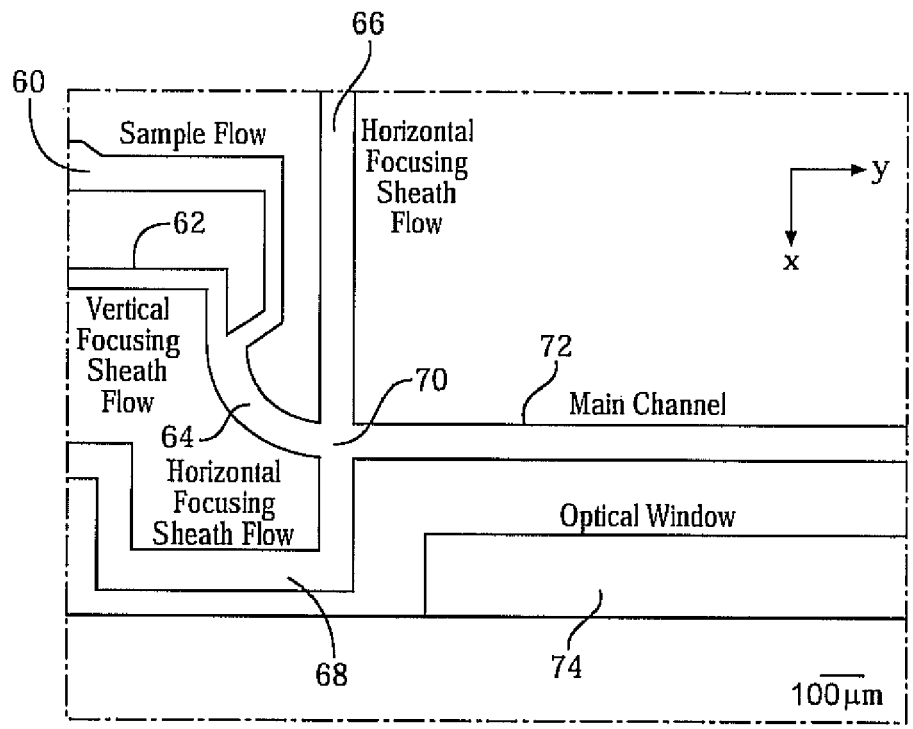
Figure 2C:
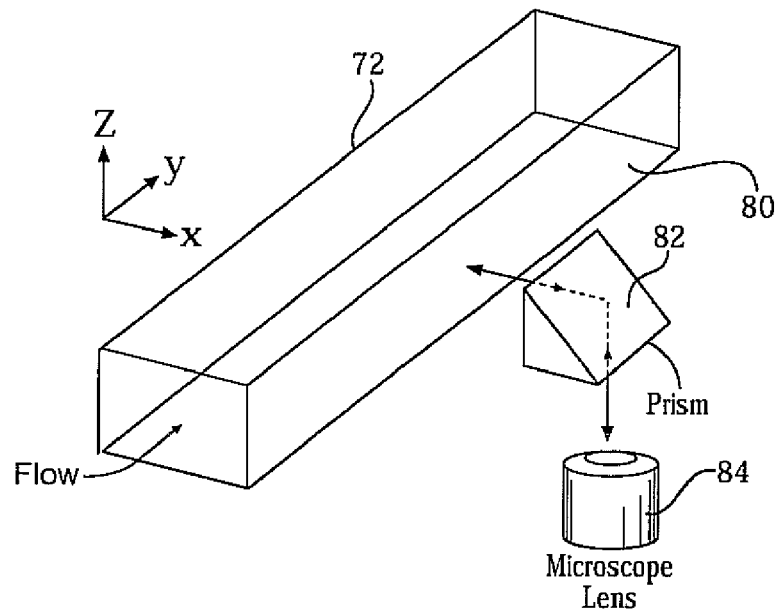

FIGS. 2A-2C show an example device design and optical setup for creating and characterizing a 3D focused flow. FIG. 2A shows the device having a sample flow inlet 54, vertical focusing sheath flow inlet 52, horizontal focusing sheath flow inlets 50 and 56, and outlet 58, and optical window 60. FIG. 2B shows a magnified detail of the hydrodynamic focusing portion, with sample flow channel 60, vertical focusing sheath flow channel 62, horizontal focusing sheath flow channels 66 and 68, and main channel 72. The main channel 72 is a portion of the outlet channel, which may be generally linear, in which hydrodynamic focusing is realized. An optical window 74, cut from window 60 as described below, allows visual access to the main channel 72.

The microfluidic channel was made by casting the PDMS on a planar silicon mold fabricated using the standard photolithography and deep reactive ion etching (DRIE). To observe the focusing in the vertical direction, a smooth, transparent optical window was placed adjacent to the main channel to allow side-view imaging of the focused flow. The PDMS substrate was cut along the "PDMS cut line" (dashed line 76 in FIG. 2A) to expose the optical window 74 to a light source (window 74 in FIG. 2B being formed from window 60 in FIG. 2A).

A 45-degree prism was placed adjacent to the optical window to deflect the excitation light and emission light so the side-view profile of the focused flow can be monitored using an epifluorescence microscope. FIG. 2C is a simplified schematic, showing part of the main channel 72 with side wall 80 visually accessible using prism 82 and microscope lens 84, the window not being shown for illustrative simplicity.

Experimentation of 3D hydrodynamic focusing was conducted as determined by the prior CFD simulations and visual evidence of 3D hydrodynamic focusing (both top-view and side-view) were obtained via epifluorescence microscopy. The fluorescein (50 µM) dyed sample flow and vertical focusing sheath flow (DI water) were co-infused into the 90-degree curve at flow rates of 50 µl/min and 337 µl/min, respectively. The horizontal focusing sheath flows (DI water) were injected from both sides at a flow rate of 225 µl/min.

Figure 3A:
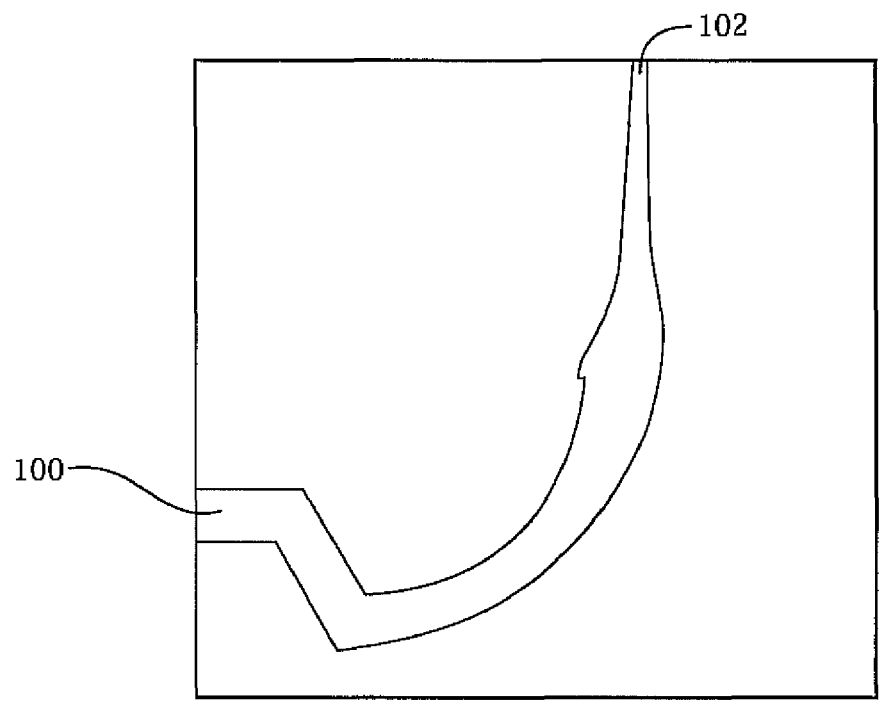
FIGS. 3A-3D illustrate sample flow patters, where

FIG. 3A depicts the top view of the fluorescent sample flow during the focusing process. The sample flow is fluorescent and shows up as the light-colored flow in this image, entering at 100 and exiting at 102. Once entering the 90-degree curve, the sample flow starts to drift to the opposite side of the channel, visually evident by the increase in the width of the sample flow. The width of the sample flow reaches its maximum at the exit of the 90-degree curve, upon which the flow is compressed by the horizontal focusing sheath flows to a horizontally focused flow at 102.

In sheath flow focusing, a central sample solution with a low flow rate flows within an outer fluid sheath traveling at a higher flow rate, thus enabling the compression of the inner sample flow. For example, both horizontally focusing sheath flows may enter the main channel at a higher speed than the sample flow.

Figure 3B:
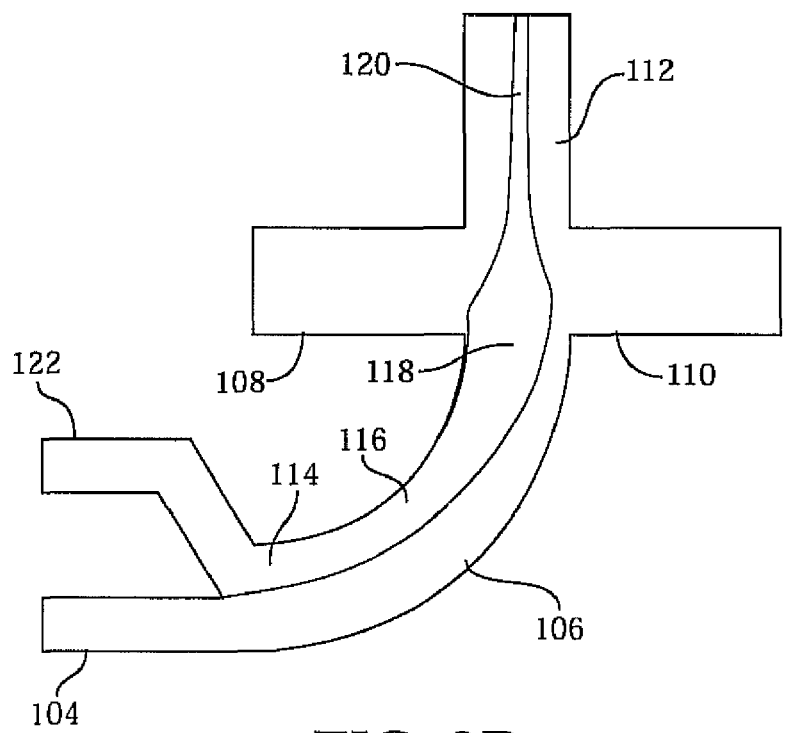

FIG. 3B shows a CFD simulation performed under conditions corresponding to the experimental conditions of FIG. 3A, which accurately replicated experimental observation. The figure shows sample flow 100, sheath flows 104, 108, and 110, and output flow 120. The sample flow is focused in the vertical direction (out of the plane of the figure) within the curved channel 106. The sample flow is widest in the horizontal direction as it exits the curved channel 106 and combines with the horizontal focusing sheath flows 108 and 110.

The horizontal focusing narrows the simulated fluorescent region to 3D focused flow at 102.

Figure 3C:
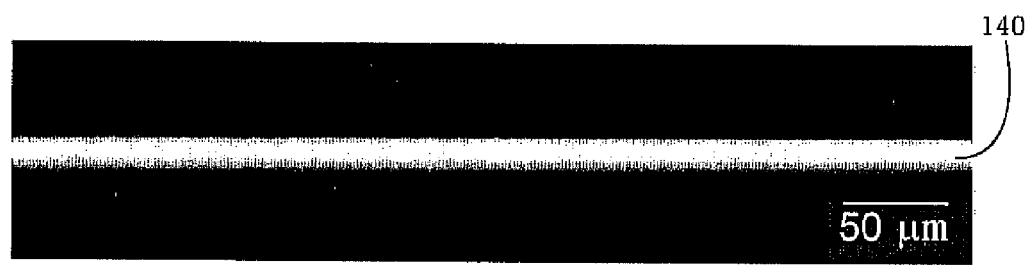

FIG. 3C depicts the side-view of the 3D focused flow 140 in the main channel. The sample flow is found to be focused in the center of channel with a total height of less than 15 μm.

Figure 3D:
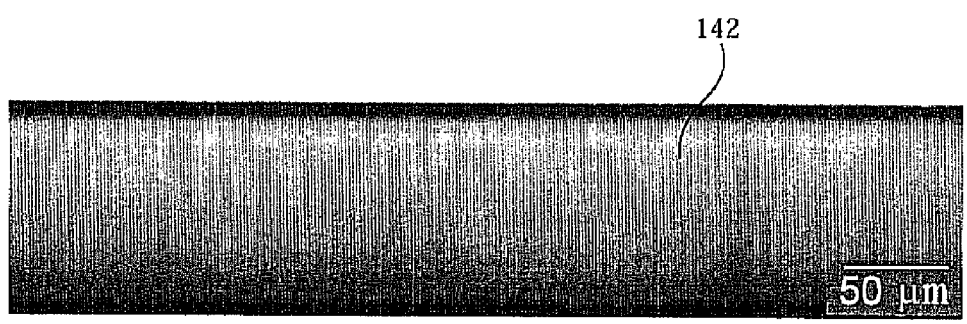

FIG. 3D shows the side-view of the main channel after the flows have been stopped. The fluorescent dye diffuses through the entire channel resulting in a uniform distribution of fluorescent dye at a much lower concentration. It was also observed that switching between static flow and 3D focusing talks less than 3 seconds and is highly repeatable Confocal microscopy was conducted in order to reveal the full 3D architecture of the sample flow in the 3D hydrodynamic focusing process. The 3D structure of the sample flow is constructed using a Z-stacked series of fluorescent images scanned at 2 μm intervals.

Figure 4A:
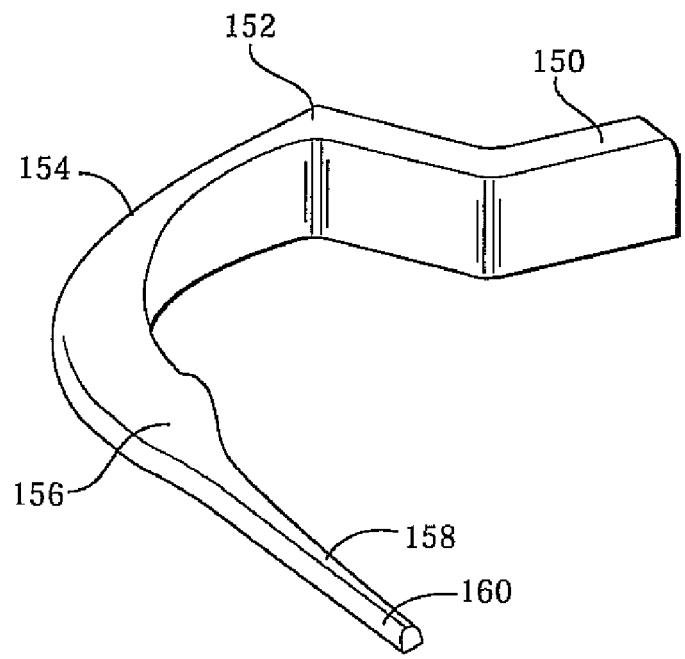
FIG. 4A shows the 3D architecture of the sample flow during the focusing process characterized by confocal microscopy.

FIG. 4A depicts the 3D image of the sample flow and clearly reveals the microfluidic drifting in the curve as well as the final 3D focused flow. The microscopy stacked image shows input sample flow at 150, joining with the vertical focusing sheath flow at 150 (the sheath flows are not fluorescent and hence do not show here), the sample flow interface with the sheath flow bending outwards within the curved channel 154. The sample flow is then focused horizontally by horizontal focusing sheathing flows incident at 156, the focusing occurring at 158 to form a narrower centralized sample flow at 160.

Figure 4B:
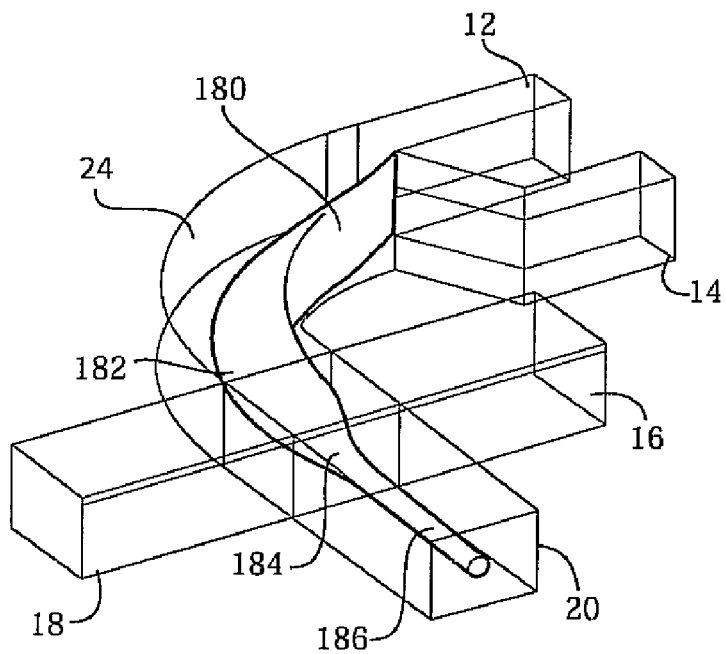
FIG. 4B shows the CFD simulation performed under the same flow conditions (an isosurface of fluorescein concentration 15 μM is arbitrarily chosen as the boundary of the sample flow)

FIG. 4B is a CFD simulation obtained with the same flow conditions. The CFD simulation was conducted using a finite-volume based commercial package, CFD-ACE+ (ESI-CFD, Huntsville, Ala.). The built-in flow module and chemistry module were used to simulate the flow and the fluorescent dye (fluorescein) distribution inside a three-dimensional (3D) focusing device. A computational grid was created using the ESI-GEOM tool of the ESI-CFD package. The grid has dimensions identical to the actual device except that only a portion of the device was modeled to reduce the computation load. The grid contains 123,000 computational cells to ensure sufficient grid density for the simulation. Strong agreement was observed between the confocal microscopic image and the simulated result.

The figure shows sample flow input 14, sheathing flow inputs 12, 16, 18, and 20, and output flow channel 20, as described in relation to FIG. 1. Initially, the sample flow and sheath flow are side by side in the channel with an approximately vertical interface, as shown at 180, but as they flow around the curved channel, the sample flow tends to locate at mid-height within the channel, with the sheathing flow moving to upper and lower regions of the sample flow. At the end of the curved channel 24, the flow profile 182 can be approximated by a sample flow between horizontal interfaces with sheathing flow above and below the sample flow. The horizontally focusing sheathing flows then tend to centralize the sample flow within the channel, as shown at 184 and 186.
Particle Focusing Small molecules (for examples, molecules on the size on the order of a few nanometers or less) can follow the sample flow streamlines and can thus be effectively focused in applications such as single molecule detection. For larger particles such as biological cells (with a diameter of several micrometers), whose density is different from that of carrier fluids, tend to deviate from the streamlines, thus may cause adverse effect to 3D hydrodynamic focusing using "microfluidic drifting". Numerical simulation and experimental validation were used to show that microfluidic drifting based 3D hydrodynamic focusing can effectively focus microparticles (including particles with size and density close to those of biological cells).

A numerical simulation of microparticle focusing process using a finite-volume (FV) based multi-physics package, ESI-CFD+ (ESI-CFD. The "flow module" and "spray module" were employed to simulate the motion of discrete particles in 3D focusing process.

Figure 5:
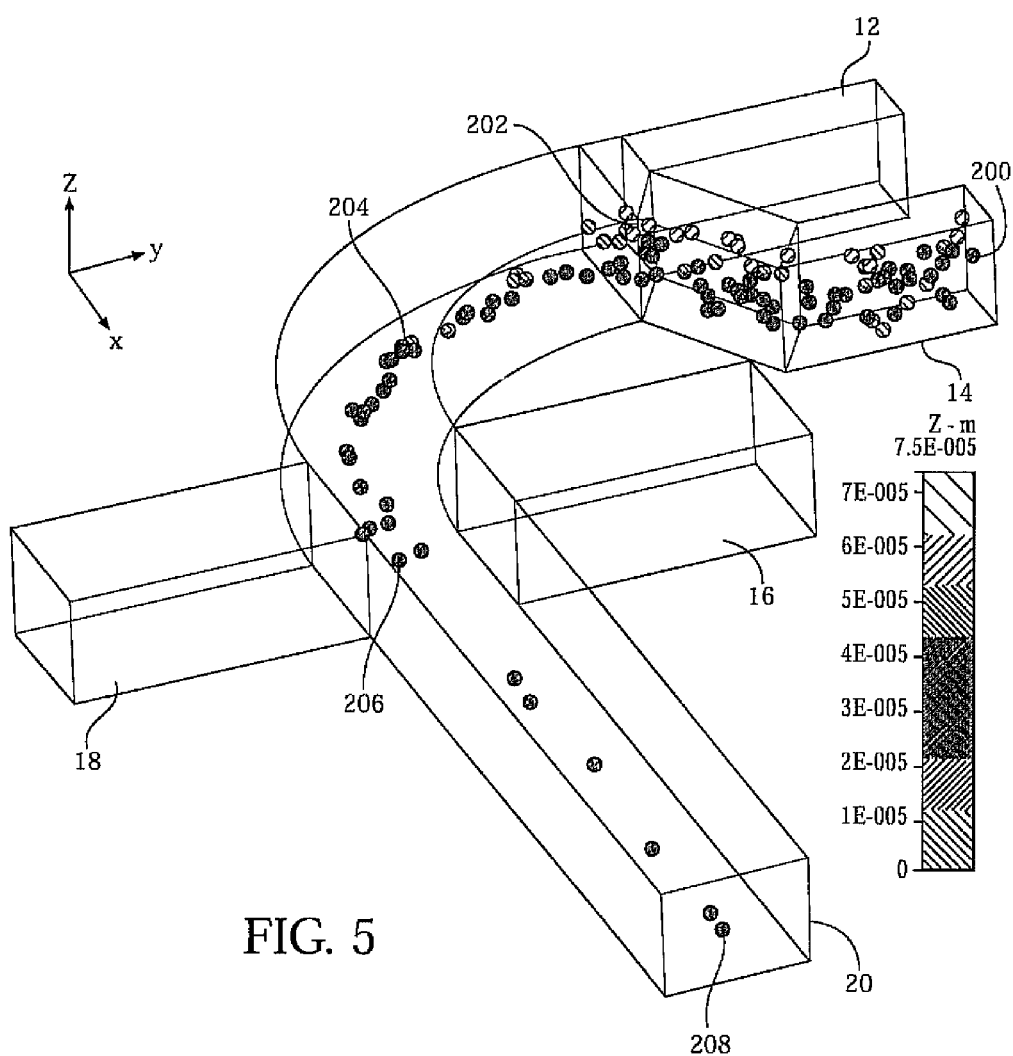
FIG. 5 illustrates hydrodynamic focusing of a sample flow comprising particles.

FIG. 5 shows a CFD simulation of 3D particle focusing process, indicating the height of individual particles. Particle sources were uniformly distributed in height at the particle inlet. The particles are shaded according to their height (Z direction, normal to the substrate). In X-Y plane, it is clearly shown that particles are lined up in the main channel. The height distribution of the particles change to approximately uniform height upon completion of 3D hydrodynamic focusing, indicating the particles are focused vertically to the center plane of the channel.

The sample flow input 14, sheathing flow inputs 12, 16, 18, and 20, and output flow channel 20 are as described in relation to FIG. 1. In this example, the input sample flow comprises particles such as 200. The vertical distribution of particles in the input flow is initially approximately random. The sample flow joins with the vertical focusing sheath flow at 202, and the drifting effect causes the particle height distribution to peak within the midpoint of the channel height. The horizontal focusing sheathing flows then centralizes the particles as shown at 208. This effect is analogous to that observed with the fluorescent sample flow discussed above.

The 3D particle focusing process was experimentally characterized with fluorescent polystyrene microparticles with size (diameter=7 μm) and density ($1.05 \times 10^3$ kg/m$^3$), similar to biological cells.

Figure 6A:
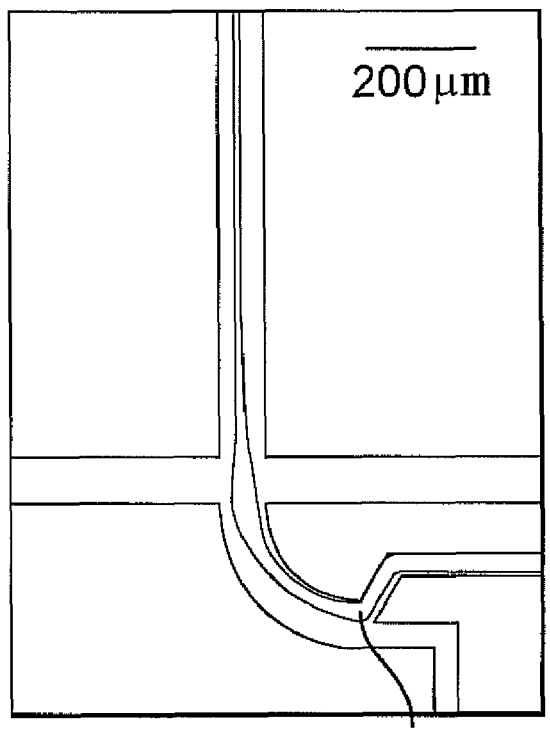
FIGS. 6A-6B are representations of fluorescent and bright field images (respectively) of 3D particle focusing.
Figure 6B:
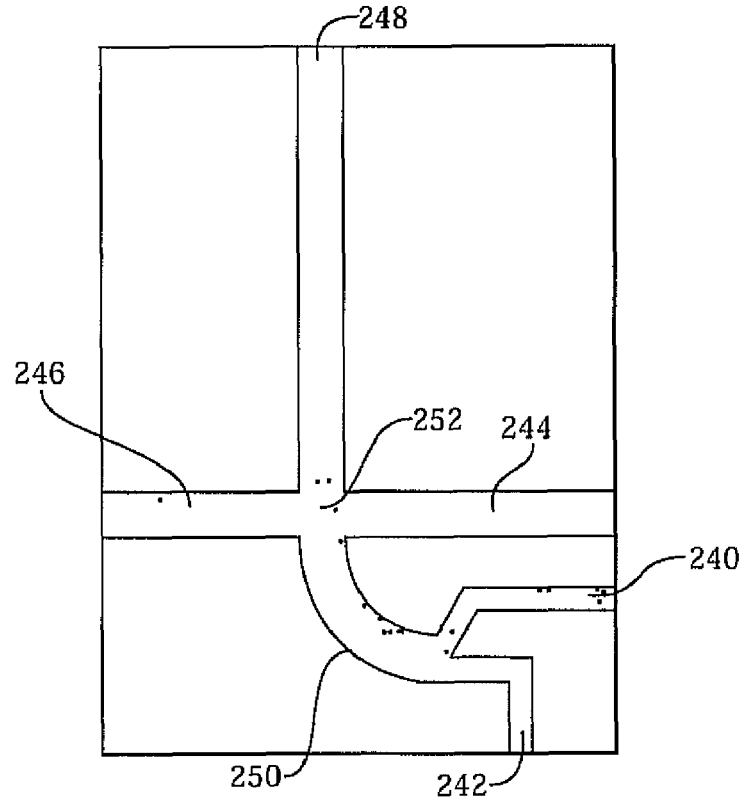

The flow patterns in both fluorescent image (FIG. 6A) and bright field image (FIG. 6B) show the "drifting" behavior of the particles in the curved channel which match the flow pattern obtained using the fluorescent dye previously described, suggesting a successfully 3D particle focusing. The image of FIG. 6A was taken over a long exposure time (200 milliseconds), showing sample flow 220. FIG. 6B shows sample flow input 240, sheathing flow inputs 242, 244, 246, and output flow channel 248.

Figure 7A:
FIGS. 7A-7B show side-view imaging of the 3D hydrodynamic focusing of microparticles.
Figure 7B:
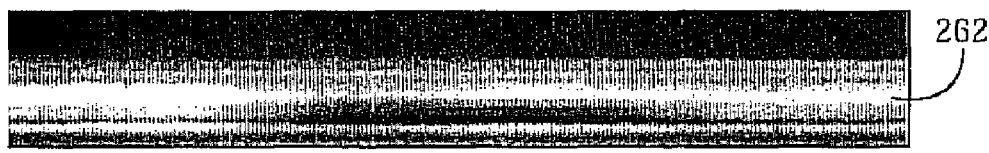

FIGS. 7A and 7B show a side-view imaging test of the 3D particle hydrodynamic focusing, conducted using the same setup as previously described above in relation to FIGS. 2-3. FIG. 7A shows that a particle can be effectively focused in the center of the channel, shown at 260. When the flow injection is stopped, the particles are not longer vertically focused and particles travel through the channel at different height, shown as the lighter region 262. Most particles travel in the region closer to channel bottom due to gravity, as compared to the previously described small fluorescein molecules which were uniformly distributed in the entire channel in FIG. 3D.

Hence, a novel "microfluidic drifting" technique can be effectively used in focusing not only small molecules, but also larger microparticles such as biological cells. A microfluidic drifting approach is readily applicable for 3D hydrodynamic focusing of biological molecules for single molecule detection as well as biological cells for microfluidics based flow cytometry devices.
Example Device Fabrication Polydimethylsiloxane (PDMS) microchannels were fabricated using a standard soft lithography technique. The master mold for the soft lithography was made on a silicon wafer (TechGophers, Chino Hills, Calif.) by Deep Reactive Ion Etching (DRIE, Adixen, Hingham, Mass.). The positive photoresist Shipley 1827 (MicroChem, Newton, Mass.) was lithographically patterned on the silicon wafer to act as a mask for DRIE, and the etch depth was set at 75 μm. The final mold depth was measured using a profilometer (KLA-Tencor, San Jose, Calif.) to ensure that the desired depth had been achieved.

The silicon mold was subsequently coated with 1H,1H,2H, 2H-perfluorooctyltrichlorosilane (Sigma Aldrich, St. Louis, Mo.) after DRIE, in order to reduce surface energy and hence the damage to the PDMS channel during the demolding process. A smooth surface of the PDMS channel sidewall reduces scattering losses and improves the quality of side-view epifluorescence microscopy. Sylgard™ 184 Silicone Elastomer Base and Sylgard™ 184 Silicone Elastomer Curing Agent (Dow Corning, Midland, Mich.) were mixed at a 10:1 weight ratio, cast onto the silicon mold, and cured at 70° C. for 2 hours. After the PDMS channel was hardened, it was peeled from the mold. Inlets and outlets were drilled with a silicon carbide drill bit and the channel was subsequently sealed onto a glass slide. Polyethylene tubes (Becton Dickson, Franklin Lakes, N.J.) were inserted into the inlets to connect the device to a syringe pump (KDS 210, KD Scientific, Holliston, Mass.).

A 2 mm×2 mm 90-degree prism (Edmund Optics, Barrington, N.J.) was placed adjacent to the optical window to reflect the excitation light (wavelength=488 nm) from the microscope lens into the microfluidic channel and the emission light (wavelength=525 nm) from the 3D focused flow downward into the microscope lens. Still images and a real-time video of the 3D focusing process were recorded using an inverted microscope (TE 2000U, Nikon, Melville, N.Y.) and a CCD camera (CoolSNAP HQ2, Photometrics, Tucson, Ariz.).

Applications

Hydrodynamic focusing is extremely useful for various microfluidics applications, such as chemical/biological analyses, including on-chip flow cytometry, single molecule detection, and laminar mixers for the study of rapid chemical and enzymatic kinetics. Improved microfabrication procedures described herein allow for three-dimensional (3D) hydrodynamic focusing devices with the ability to focus the sample flow in the vertical direction, and allow 3D on-chip manipulation of the sample flow.

The planar nature of a microfluidic network fabricated via standard soft lithography only facilitates two-dimensional (2D) hydrodynamic focusing using horizontally (in-plane) compression of the inner sample flow into a thin "sheet" between two sheath flows injected from both sides of the sample flow. There is no ability to focus the sample flow in the vertical (out-of-plane) direction. 3D focusing may be achieved by delivering sheath flows from both vertical and horizontal directions using a multi-layer microfluidic device. Such methods require either tedious assembly of individual components or multiple alignments and exposures during mold fabrication. These limitations significantly increase the cost and complexity of the device and ultimately severely hinder their applicability.

For many applications, 2D hydrodynamic focusing alone is intrinsically problematic due to the lack of vertical focusing. For example, the non-uniform velocity distribution of vertically spread cells or molecules is known to cause problems in flow cytometry.

A microfluidic device according to the present invention may be an analytical instrument, such as a spectrometer, for example a fluorescence spectrometer or a laser spectrometer. A microfluidic device may further be a flow cytometer, laminar mixer, a reaction vessel, or a chemical processing device.

Three-dimensional hydrodynamic focusing is useful for microfluidics-based flow cytometry system. In conventional flow cytometry, 3D hydrodynamic focusing is achieved using a co-axial structure. However, such structures are difficult to implement using the standard soft-lithography technique, which only facilitates the 2D planar fluidic structures. However, the novel hydrodynamic focusing technique using microfluidic drifting enables 3D hydrodynamic focusing in a single-layer two-dimensional (2D) planar microfluidic structure, something never before achieved in conventional microfluidic devices. 3D hydrodynamic focusing can be achieved for molecular solutions, as shown using a fluorescent dye solution, and the same approach can be used for the SD focusing of discrete microparticles, such as lymphocytes which are routinely screened in HIV diagnosis using flow cytometry.

Novel 3D focusing techniques described herein are particularly useful for on-chip single molecule detection, which requires passage of the sample through an optical detection region that is much smaller than the channel size. In conventional microfluidic devices, the vertical spread of sample results in a large number of undetected molecules. However, the vertical focusing provided by examples of the present invention avoids such problems, and allows accurate single molecule detection, Other Aspects Examples of the invention include novel apparatus and methods to implement three dimensional (3D) hydrodynamic focusing using a single-layer planar microfluidic device, which can be fabricated using a standard soft-lithography technique.

An improved microfluidic device comprises a curved channel section operable to focus a sample flow in an out-of-plane direction, compressing the flow in a direction generally normal to a plane including the curved channel (such as a plane parallel to the substrate). An improved microfluidic device operable to provide three-dimensional hydrodynamic focusing of a sample flow uses a vertical focusing sheath flow and at least one horizontal focusing sheath flow, flows being generally coplanar and being conveyed within channels of a planar device. Unlike conventional devices, no out-of-plane sheath flow or multilayer structures are required.

Embodiments of the present invention include improved flow cytometers and other cell characterization devices, improved single molecule detection devices, other analyte characterization devices, analyte sorting devices, genetic analysis devices, and the like. An analyte may be a molecule (such as a small molecule, polymer, biomolecule), biological structure (such as a cell, for example a blood cell), particle (of any type), and the like. A radiation beam, such as a laser, may be directed through the narrow portions of a focused flow. Scattering, fluorescence, or other property may be monitored.

In a laminar mixer, flow velocity variations of the focused enzymes or chemical species in the vertical direction may result in a different reaction time across the depth of the channel, which would make it extremely difficult to extract meaningful information of reaction kinetics. Hence, an improved laminar mixer according to an embodiment of the present invention includes a curved channel for inducing hydrodynamic focusing.

An example microfluidic device, operable to provide three-dimensional hydrodynamic focusing of a sample flow, includes a first channel having a curved channel section operable to provide hydrodynamic focusing of the sample flow in a direction out of a plane including the curved channel. The device may be a planar microfluidic device. The device may further include a second channel crossing the first channel, the second channel operable to convey a sheath flow inducing in-plane hydrodynamic focusing of the sample flow.

Example apparatus according to the present invention include a flow cytometer, a fluorescence spectrometer, a laser spectrometer, a laminar mixer, a reaction vessel, or a chemical processing device. Other examples will be apparent to those skilled in the art.

A curved channel within an improved apparatus may, for example, have a generally rectangular or square cross-section. The channel width and/or height may be in the range 100 nm-1 mm, for example in the range 1 micron-500 microns. The mean radius of the curved channel may be in the range 1 micron-1 mm, for example in the range 10 microns-500 microns. The curved channel may have a lower wall parallel to and proximate the substrate, a curved inner side wall, a curved outer side wall (the outer side wall having a radius of curvature greater than the inner side wall), and an upper wall opposite the lower wall and generally parallel to the substrate. The terms upper and lower are used for illustrative simplicity and are not intended to be limiting. The sample flow and first sheath flow may be introduced so that the sample flow is initially closer to the inner wall. The fluid interface between the sample flow and the first sheath flow may initially be vertical (as used in this example, the term vertical refers to a direction normal to the substrate). However, as the sample flow and the first sheath flow pass through the curved channel, the fluid interface tends to curve outwards, towards the outer wall, for example as discussed in relation to FIG. 1. At the end of the curved channel, it is possible to obtain a sample flow centered between the upper and lower walls, with the first sheath flow split into a layer further from the substrate and a layer nearer the substrate than the sample flow. The sample flow is compressed so as to be a layer extended generally parallel to the substrate, and may be centered in the channel along a vertical direction. Hence, the sample flow becomes compressed (narrowed) as measured along a direction normal to the substrate, which may be termed vertical hydrodynamic focusing, though the term "vertical" here represents a direction normal to the substrate and is not otherwise intended to be limiting.

An example microfluidic device includes a first channel having a curved channel section, the curved channel section being operable to provide hydrodynamic focusing in a focus plane, the focus plane being non-parallel to a plane including the curved channel section. The device may include a substrate, the focus plane being generally normal to the substrate. The device may have an inlet for a sample flow, and an inlet for a vertical focusing sheath flow. The device may further including a second channel crossing the first channel, the second channel having at least one inlet for a horizontal focusing sheath flow.

A method of three-dimensional hydrofluoric focusing of a sample flow comprises passing the sample flow and a first sheath flow through a curved channel section; and passing the sample flow through a second sheath flow, the second sheath crossing the sample flow, the curved channel section and second sheath flow cooperatively providing three-dimensional hydrofluoric focusing of the sample flow.

A method of hydrofluoric focusing a sample flow in a planar microfluidic device having a planar substrate comprises passing the sample flow and a sheath flow through a curved channel section disposed on the planar substrate, the curved channel section providing hydrofluoric focusing of the sample flow in a direction generally normal to the planar substrate. The method may further comprise hydrofluoric focusing in an in-plane direction, for example using a pair of sheath flows within a linear flow channel.

A further example of the present invention is an apparatus comprising a plurality of 3D hydrodynamic focusing components, and in some example two or more focused sample flows may intersect or otherwise interact.

Examples of the present invention include apparatus and methods for flow cytometry, and apparatus for counting, analysis, and sorting of particles in the sample flow (e.g. microscopic particles such as cells, molecules, biomolecules, and the like) suspended in the sample flow. Particles may be labeled, for example with a fluorescent marker, or otherwise functionalized. For example, biological macromolecules may be fluorescently tagged and detected in the sample flow.

Example apparatus may include a radiation source (such as a laser), and a radiation beam may be directed into the main channel at or proximate the point of hydrodynamic focus. One or more detectors may be configured to receive detected radiation, which may comprise transmitted, scattered and/or fluorescent radiation. An electronic circuit, such as a computer, may be used to analyze detector signals, so as to determine properties of the particles. For example, cell dimensions and other properties may be determined, and particles may be imaged, reacted, or otherwise processed.

Examples of the present invention include high-throughput cell cytometers, single-molecule fluorescent spectrometers, genetic analyzers, fluorescence-activated cell sorters, and other applications. In some examples, particles having detected properties may be counted, extracted, sorted, or otherwise processed. In some examples, a plurality of radiation sources, such as lasers, and associated detectors may be used.

An example microfluidic device is operable to provide three-dimensional hydrodynamic focusing of a sample flow using a first (vertical) focusing sheath flow and one or more horizontal focusing sheath flows, the sample flow, vertical focusing sheath flow and the horizontal focusing sheath flow(s) being generally coplanar. This enables the device to be more simply fabricated than previous approaches, for example as a single layer device in which all flow channels may be generally coplanar.

The invention is not restricted to the illustrative examples described above. Examples are not intended as limitations on the scope of the invention. Methods, apparatus, compositions, and the like described herein are exemplary and not intended as limitations on the scope of the invention. Changes therein and other uses will occur to those skilled in the art. The scope of the invention is defined by the scope of the claims.

Having described our invention, we claim:

1. An apparatus, the apparatus being a microfluidic device comprising:
  a substrate, the substrate being generally planar;
  a sample flow inlet, configured to receive a sample flow;
  a first flow inlet, configured to receive a first sheath flow; and
  a curved channel, the curved channel configured to receive the sample flow and the first sheath flow,
  the sample flow inlet, the first flow inlet, and the curved channel being supported by the substrate, the curved channel being generally parallel to the substrate,
  the curved channel being configured to provide out-of-plane hydrodynamic focusing of the sample flow when the sample flow and first sheath flow pass together through the curved channel,
  the sample flow being compressed along a direction normal to the substrate,
  the apparatus further comprising inlets for in-plane hydrodynamic focusing sheath flows, the in-plane hydrodynamic focusing sheath flows providing hydrodynamic focusing of the sample flow along a direction parallel to the substrate, the first sheath flow together with the in-plane hydrodynamic focusing sheath flows providing three-dimensional hydrodynamic focusing of the sample flow.

2. The apparatus of claim 1, the sample flow, the first sheath flow, and the in-plane hydrodynamic focusing sheath flows being substantially co-planar.

3. The apparatus of claim 1, the apparatus being operable to provide the three-dimensional hydrodynamic focusing within an output channel, the sample flow being compressed near the center of the output channel.

4. The apparatus of claim 3, further comprising a radiation detector configured to detect radiation from the sample flow within the output channel.

5. The apparatus of claim 4, further comprising an excitation source configured to induce the radiation within the sample flow.

6. The apparatus of claim 1, the apparatus being a microfluidic device, the microfluidic device being a component of a flow cytometer, a fluorescence spectrometer, a laser spectrometer, a laminar mixer, a reaction vessel, or a chemical processing device.

7. The apparatus of claim 1, the apparatus being a single-layer planar microfluidic device.

8. The apparatus of claim 1, the curved channel having a bend angle of approximately 90 degrees.

9. The apparatus of claim 1, the curved channel having an inner side wall and an outer side wall, the side walls being generally normal to the substrate, the sample flow inlet and the first flow inlet being configured to introduce the sample flow and first sheath flow into the curved channel so as to initially have a fluid interface generally parallel to the side walls, the fluid interface between the sample flow and first sheath flow becoming curved as the sample flow progresses along the curved channel, the sample flow leaving the curved channel as a layer narrowed in a direction normal to the substrate, the first sheath flow leaving the curved channel split into layers closer to and further away from the substrate relative to the sample flow.

10. The apparatus of claim 9, the sample flow being introduced to the curved channel so as to be initially closer to the inner side wall.

11. An apparatus, the apparatus being a planar microfluidic device configured to receive a sample flow and a first sheath flow, the apparatus having a sample flow inlet for the sample flow, and a first sheath inlet for the first sheath flow, the apparatus including a curved channel supported by and generally parallel to a planar substrate, the sample flow inlet and first sheath inlet introducing the sample flow and the first sheath flow into the curved channel, the curved channel being configured to provide out-of-plane hydrodynamic focusing of the sample flow, the sample flow being compressed in a direction normal to the planar substrate, the apparatus further including at least one inlet for an in-plane focusing sheath flow, the first sheath flow and the in-plane hydrodynamic focusing sheath flows together providing three-dimensional hydrodynamic focusing of the sample flow.

12. The apparatus of claim 11, the sample flow and the first sheath flow having a fluid interface that is generally normal to the substrate as the sample flow and first sheath flow are introduced to the curved channel.

13. The apparatus of claim 11, the apparatus including a linear channel section configured so that the sample flow passes through the linear channel section between a pair of in-plane focusing sheath flows.

14. A method of hydrofluoric focusing a sample flow in a planar microfluidic device having a planar substrate, the method comprising:

passing the sample flow and a sheath flow through a curved channel section disposed on the planar substrate, the curved channel section providing hydrofluoric focusing of the sample flow in a direction generally normal to the planar substrate, and passing the sample flow through a linear channel section between a pair of in-plane focusing sheath flows so as to obtain three-dimensional hydrofluoric focusing of the sample flow.

15. The method of claim 14, the sample flow, the sheath flow, and the pair of in-plane focusing sheath flows being generally coplanar.

16. The method of claim 15, the sample flow including biological cells, the method including hydrodynamic focusing of the biological cells within the sample flow to facilitate detection of the biological cells using flow cytometry.

17. The method of claim 15, the sample flow including fluorescent molecules, the method including hydrodynamic focusing of the fluorescent molecules to facilitate detection of the fluorescent molecules using single-molecule fluorescence spectroscopy.

* * * * *

UNITED STATES PATENT AND TRADEMARK OFFICE
CERTIFICATE OF CORRECTION

PATENT NO.         : 8,120,770 B2
APPLICATION NO.    : 12/207699
DATED              : February 21, 2012
INVENTOR(S)        : Tony Jun Huang et al.

Page 1 of 1

It is certified that error appears in the above-identified patent and that said Letters Patent is hereby corrected as shown below:

Column 10, line 14 should read 3D.

Signed and Sealed this
Second Day of October, 2012

David J. Kappos
*Director of the United States Patent and Trademark Office*

UNITED STATES PATENT AND TRADEMARK OFFICE
CERTIFICATE OF CORRECTION

PATENT NO. : 8,120,770 B2
APPLICATION NO. : 12/207699
DATED : February 21, 2012
INVENTOR(S) : Tony Jun Huang et al.

It is certified that error appears in the above-identified patent and that said Letters Patent is hereby corrected as shown below:

Col. 1, lines 14-17: replace "This invention was made with government support under awarded by Contract No. ECCS-0609128 awarded by the National Science Foundation. The government has certain rights in the invention."

with

-- This invention was made with government support under Grant Nos. ECCS0609128 and ECCS0824183, awarded by the National Science Foundation and Grant No. OD007209, awarded by the National Institutes of Health. The Government has certain rights in the invention. --

Signed and Sealed this
Fourth Day of December, 2012

David J. Kappos
*Director of the United States Patent and Trademark Office*